United States Patent [19]
Akimoto et al.

[11] Patent Number: 5,834,512
[45] Date of Patent: Nov. 10, 1998

[54] PREVENTION AND IMPROVEMENT OF ALLERGY CAUSED BY LEUCOTRIENE B 4

[75] Inventors: Kengo Akimoto, Osaka; Hiroshi Kawashima; Satomichi Yoshimura, both of Takatsuki; Masashi Matsui, Suita; Tomohito Hamazaki; Shigeki Sawazaki, both of Toyama; Norio Nakamura, Nei-gun, all of Japan

[73] Assignee: Suntory Limited, Osaka, Japan

[21] Appl. No.: 688,017

[22] Filed: Jul. 29, 1996

Related U.S. Application Data

[63] Continuation of Ser. No. 249,996, May 27, 1994, abandoned.

[30] Foreign Application Priority Data

May 28, 1993 [JP] Japan ................................. 5-127031
May 26, 1994 [JP] Japan ................................. 6-112800

[51] Int. Cl.⁶ .................................................. A61K 31/20
[52] U.S. Cl. ......................................................... 514/560
[58] Field of Search ............................................. 514/560

[56] References Cited

U.S. PATENT DOCUMENTS

| | | | |
|---|---|---|---|
| 4,432,906 | 2/1984 | Cohen et al. | 260/410.9 R |
| 4,434,101 | 2/1984 | Cohen et al. | 260/410.9 R |
| 4,877,789 | 10/1989 | Shroot et al. | 514/255 |
| 5,066,427 | 11/1991 | Shroot et al. | 260/413 |
| 5,130,147 | 7/1992 | Karu | 426/2 |
| 5,210,208 | 5/1993 | Huang et al. | 548/253 |
| 5,260,336 | 11/1993 | Forse et al. | 514/560 |
| 5,322,780 | 6/1994 | Kawashima et al. | 435/134 |
| 5,376,541 | 12/1994 | Kawashima et al. | 435/136 |

FOREIGN PATENT DOCUMENTS

| | | |
|---|---|---|
| 0 209 770 | 1/1987 | European Pat. Off. . |
| 0 260 655 | 3/1988 | European Pat. Off. . |
| 61-204136 | 9/1986 | Japan . |
| 62-129241 | 6/1987 | Japan . |
| 62-195346 | 8/1987 | Japan . |
| 1-019040 | 1/1989 | Japan . |
| 1-026532 | 1/1989 | Japan . |
| 1-190656 | 7/1989 | Japan . |
| 4-244023 | 9/1992 | Japan . |
| 5-310668 | 11/1993 | Japan . |
| 5-91888 | 12/1993 | Japan . |
| 6-502164 | 3/1994 | Japan . |
| WO92/05145 | 4/1992 | WIPO . |
| 94/21247 | 9/1994 | WIPO . |

OTHER PUBLICATIONS

Nguyen et al, "New Model of a Scaling Dermatosis: Induction of Hyperproliferation in Hairless Mice with Eicosa–5, 8,11–Trienoic Acid", *J. Invest. Dermatol.*, vol. 76(5), pp. 384–387, (1981).

Stenson et al, "Leukotriene B Formation By Neutrophils From Essential Fatty Acid–deficient Rats", *J. Bio. Chem.*, vol. 259(19), pp. 11784–11789 (1984).

Adkisson et al, "Unique Fatty Acid Composition of Normal Cartilage: Discovery of High Levels of n–9 Eicosatrienoic Acid and Low Levels of n–6 Polyunsaturated Fatty Acids", *Faseb J.*, vol. 5(3), pp. 344–353 (1991).

James et al, Effect of Dietary Supplementation with N–9 Cicosatrienoic Acid on Keukotriene B4 Synthesis in Rats: A Novel Approach to Inhibition of Eicosanoid Synthesis, *J. Exp. Med.*, vol. 178(6), pp. 2261–2265 (1993).

Jakschik et al, "Products Derived from 5,8,11–Eicosatrienoic Acid by the 5–Lipoxygenase–Leukotriene Pathway," *J. Bio. Chem.*, pp. 12797–12800 (1983).

Lefkowith et al, "Manipulation of the Acute Inflammatory Response by Dietary Polyunsaturated Fatty Acid Modulation", *J. Immun.*, vol. 145(5), pp. 1523–1529 (1990).

Marone et al, "An Inhibitor of Lipoxygenase Inhibits Histamine Release from Human Basophils," *Clinical Immun. and Immunopathology*, vol. 17, pp. 117–120 (1980).

*Primary Examiner*—William R. A. Jarvis
*Attorney, Agent, or Firm*—Burns, Doane, Swecker & Mathis, L.L.P.

[57] ABSTRACT

A composition such as foods, drinks, pharmaceutical composition, for prevention or improvement of allergy, comprising an omega 9 series unsaturated fatty acid such as 6,9-octadecadienoic acid, 8,11-eicosadienoic acid, 5,8,11-eicosatrienoic acid etc.

20 Claims, 1 Drawing Sheet

PREVENTION AND IMPROVEMENT OF ALLERGY CAUSED BY LEUCOTRIENE B 4

This application is a continuation of application Ser. No. 08/249,996, filed May 27, 1994, now abandoned.

BACKGROUND OF INVENTION

1. Field of Invention

The present invention relates to a composition for prevention or improvement of medical symptoms caused by leucotriene B4 ($LTB_4$), comprising as an effective ingredient an omega 9 series unsaturated fatty acid. More specifically, the present invention relates a composition for prevention or improvement of inflammation, especially chronic inflammation such as rheumatoid arthritis, or allergy, comprising at least one effective ingredient selected from the group consisting of 6,9-octadecadienoic acid, 8,11-eicosadienoic acid and 5,8,11-eicosatrienoic acid.

2. Related Art

Inflammation is a defence reaction of organisms caused by a physical or chemical stimulation, immunological phenomena involving antibodies, immune complex, degradation products of complements, or the like. During the inflammation, characteristic phenomena occur including expansion and perforation of microvessels, leak of blood components into spaces between tissues, migration of leucocytes to an inflammatory tissue, and the like, resulting in symptoms such as erythema, edema, hyperalgesia, ache etc. In a process of inflammation, various pharmacologically active substances are locally formed and liberated, and mediate inflammatory reactions. These substances are called chemical mediators of inflammation, and include plasmakinins such as bradykinin, serotonin, histamines and the like, prostaglandin (PG), leucotriene (LT), various leucocyte migration enhancement factors, and the like.

Allergy is a condition wherein reaction harmful to an organism, such as destruction and abnormal reaction of tissue results from an immune response. In the allergy process, it is known that an allergen invades an organism and reacts with IgE antibody fixed to mast cell or basophilic leukocyte resulting in liberation of a chemical transmitter such as histamines, leucotriene (LT), eosinophilic migration enhancement factor, neutrophilic migration enhancement factor, and the like, providing cell infiltration, destruction of tissues, contraction of smooth muscle, stimulation of vascular permeability, stimulation of mucous secretion etc.

Generally, although anti-inflammatory drugs are used for inhibiting inflammatory symptoms and alleviating destruction of tissues, in the broad sense, they include allergic reaction inhibitory drugs (anti-allergic drugs). Currently available anti-inflammatory drugs are classified as steroidal anti-inflammatory drugs (adrenocortical hormones) and non-steroidal anti-inflammatory drugs. Although the steroidal anti-inflammatory drugs provide strong anti-inflammatory action, they also exhibit strong side-effects, and therefore determination of termination of and method for administration is difficult. On the other hand, although acidic non-steroidal anti-inflammatory drugs such as aspirin, indomethacin etc. exhibit anti-inflammatory action by lowering cycloxygenase activity and inhibiting PG synthesis, and are used as frequently as antibiotics and lanking after steroidal drugs, they provide side effects such as gastrointestinal injurys, nephrotoxicity, hemopoietic disorders, and therefore their use is very limited.

A more recent approach to the moderation of inflammatory and hypersensitivity responses has focused on blocking the action of arachidonic acid metabolites (including the prostaglandins), lipoxygenases and the leukotrienes. The leukotrienes (LT) metabolites are formed by oxygenation of a lipoxygenase (5-hydroperoxytetraenoic acid (5-HPETE)) which is formed by the specific oxygenation of the C-5 position of arachidonic acid. The first leukotriene formed in the metabolic pathway is the unstable epoxide intermediate leukotriene $A_4$ ($LTA_4$) which is the precursor to the family of peptide-leukotrienes, the first in the pathway being $LTC_4$ which is formed by glutathione addition. $LTC_4$ is transformed subsequently into $LTD_4$ and $LTE_4$ by successive elimination of a glutamyl and glycine residue. The peptidoleukotrienes primarily act on smooth muscle and other cells having contractile capacity, as well as playing a key role in hypersensitivity reactions. In addition, the peptido-leukotrienes are spasmogens, increase vascular permeability, activate airway smooth muscle, stimulate mucous secretion and are involved with the pathogenesis of certain inflammatory diseases such as bronchitis, ectopic and atopic eczema and psoriasis. Leukotrienes appear to be involved in the pathogenesis of asthma such as allergic pulmonary disorders of asthma, hay fever and allergic rhinitis. In addition, $LTC_4$, $LTD_4$ and $LTE_4$ may also decrease blood pressure by an action on the heart, because they reduce myocardial contractility and coronary blood flow.

Another family of leukotrienes, the $LTB_4$, is derived from $LTA_4$ by hydrolase-catalyzed addition of water. This 5,12-dihydroxy derivative, causes adhesion and chemotactic movement of leukocytes, stimulates aggregation, enzyme release and generation of superoxide in neutrophils. Additionally, $LTB_4$ is a potent chemotactic and chemokinetic agent for eosinophils, macrophages and monocytes, stimulates suppressor T lymphocytes and enhances natural cytotoxic cell activity. $LTB_4$ is also a potent (indirect) bronchoconstrictor but in contrast to the peptido-leukotrienes $C_4$, $D_4$ and $E_4$ does not appreciably stimulate mucous production and induce edema of the airways by increasing vascular permeability.

It has been suggested that compounds antagonizing $LTB_4$ activity may be valuable in the treatment of inflammatory diseases caused by tissue degrading enzymes and reactive chemicals liberated by tissue-infiltrating and aggregating polymorphonuclear leukocytes.

For example, PCT Japanese National Publication No. 6-502164 describes that novel monocyclic or bicyclic aryl compounds are selectively antagonistic to $LTB_4$ and are useful for treatment of rheumatoid arthritis, gout, psoriasis and inflammatory bowel disease. Japanese Unexamined Patent Publication (Kokai) No. 4-244023 describes that ω6 series unsaturated fatty acids such as dihome-γ-linolenic acid are useful for treatment of arrhythmia, acute myocardial infarction etc. by inhibiting production of $LTB_4$. Japanese Unexamined Patent Publication No. 5-310668 describes that a novel leucine derivative has an inhibitory action to $LTA_4$ hydrolase and are useful for treatment and prophylaxis of allergic diseases such as bronchial asthma, various inflammatory diseases, ischemia-reperfusion disorders. Japanese Unexamined Patent Publication (Kokai) No. 1-190656 discloses that novel leucotriene $B_3$ dimethyl amide has an antagonistic action to $LTB_4$ and is useful as anti-inflammatory drug, anti-rheumatic drug and gout-treatment drug.

On the other hand, it is known that 8,11-cis-eicosadienoic acid and 5,8,11-cis-eicosatrienoic acid (mead acid), which are omega 9 series fatty acids, are produced in animal tissues deficient in essential fatty acids. J. Biolog Chem. Vol. 259, No. 19, pp.11784–11789 (1984) discloses that in neutrophile of rat fed on essential fatty acid deficient feed, mead acid was detected, which was not detected in rat fed on normal feed, and an amount of $LTB_4$ decreased. However, this phenomenon is under a specific condition of essential fatty acid deficiency, and it is not clear whether mead acid alone inhibits the production of $LTB_4$ and exhibits anti-inflammatory or anti-allergic action.

In addition, Japanese Unexamined Patent Publication No. 62-129241 describes that a particular ester or amide of 5,8,11-eicosatriynoic acid inhibits the metabolism of arachidonic acid caused by cyclooxygenase and lypoxygenase. U.S. Pat. No. 4,432,906 describes that 10,10-dimethyl-5,8,11-eicosatrienoic acid and 10-methyl-5,8,11-eicosatrienoic acid are useful as anti-allergic drug and anti-asthma drug because they do not inhibit the synthesis of PG, but inhibit the synthesis of SRS-A. U.S. Pat. No. 4,434,101 describes that 7,7-dimethyl-5,8-eicosadienoic acid and 7-methyl-5,8-eicosadienoic acid are useful as anti-allergic agent and anti-asthma drug because they do not inhibit the synthesis of PG and inhibit the synthesis of SRS-A. However, it is not clear whether or not omega 9 series unsaturated fatty acid such as mead acid has $LTB_4$ production inhibitory action and is useful as prophylactic or improving drugs for inflammation, especially chronic inflammation such as rheumatoid arthritis, and allergy.

Arthritic rheumatism a chronic polyinflammatory disease, and in the serum and synovial fluid of rheumatoid arthritis patients rheumatoid factor which is an autoantibody reactive with immunoglobulin IgG is detected. Because of the presence of the rheumatoid factor, it is considered that the rheumatoid arthritis involves immune disorder. However, the cause of the disease is not known. In the treatment of rheumatoid arthritis, non-steroidal anti-inflammatory drugs are used for symptomatic therapy through the entire disease process.

SUMMARY OF THE INVENTION

The present invention provides a pharmaceutical composition effective as a prophylactic or improving drug for medical symptoms caused by $LTB_4$, especially anti-inflammatory drugs and anti-allergic drugs, and which exhibits relatively low side effects and is applicable to chronic symptoms.

The present inventors carried out researches on various unsaturated fatty acids to accomplish the above-mentioned object, and found omega 9 series unsaturated fatty acids which have high $LTB_4$-production inhibitory action and are highly useful for prophylaxis and improvement of medical symptoms caused by $LTB_4$, and completed the present invention.

DETAILED DESCRIPTION OF THE INVENTION

Figure 1:
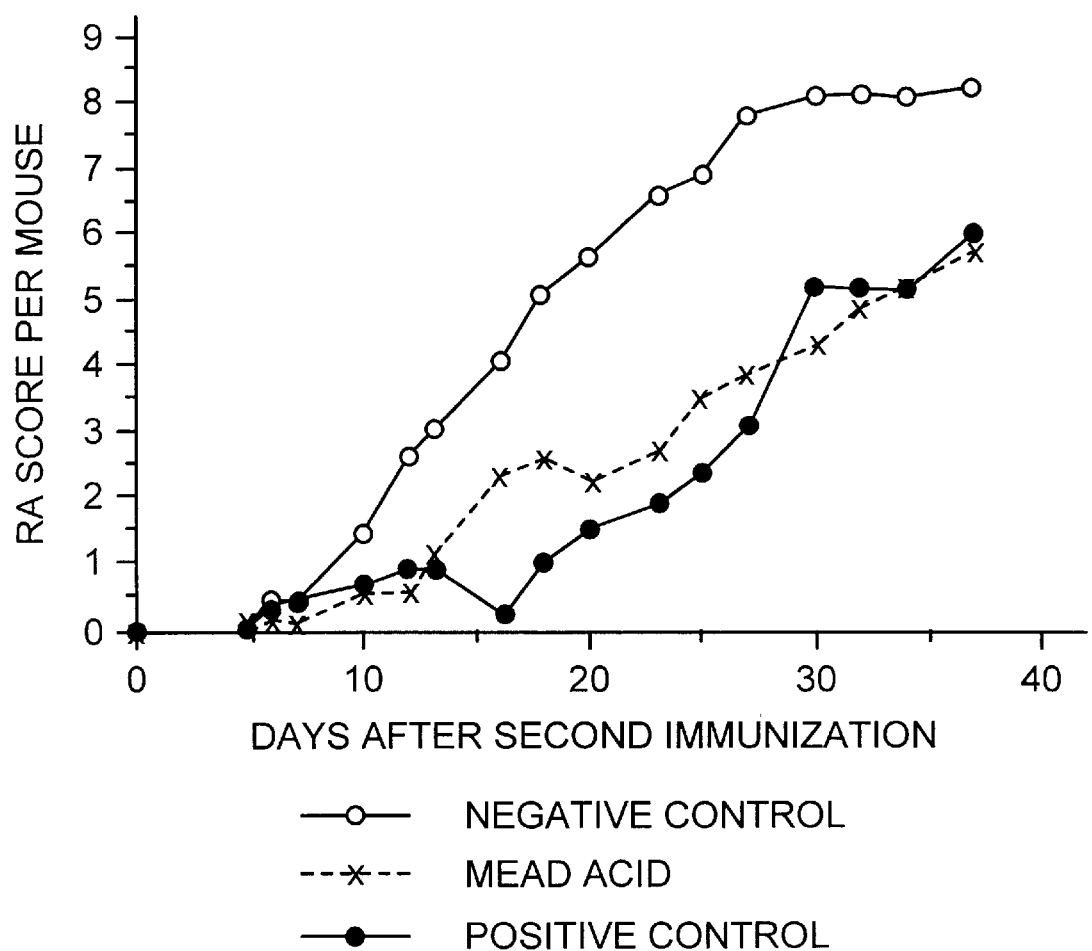
FIG. 1 shows an effect of mead acid in a collugen-induced arthritis mead.

An effective ingredient of the present composition, omega 9 series unsaturated fatty acid is a fatty acid wherein the double bond nearest to the methyl terminus of the fatty acid molecule located between the ninth carbon atom and the tenth carbon atom calculating from the terminal methyl group, having at least two double hands and preferably having 18 to 22 carbon atoms, and is for example, 6,9-octadecadienoic acid, 8,11-eicosadienoic acid, 5,8,10-eicosatrienoic acid etc. These fatty acids can be used alone or in combination. Since all of the naturally occurring omega 9 series unsaturated fatty acids are cis-type, in the present invention cis-type omega 9 series unsaturated fatty acids are preferably used. According to the present invention, the omega 9 series unsaturated fatty acids can be used not only in a form of a free fatty acid, but also in a form of salts, for example, salts of alkaline metal such as sodium, potassium, lithium or other alkaline metal, salts of other metals such as alkaline earth metal, such as zinc, calcium or magnesium, and in a form of mono-, di- or tri-glyceride, esters of lower alcohols, phospholipid, glycolipid, or amides, and especially ethyl ester and triglycerides are preferred. Here, the lower alcohol means monohydric alcohol having up to 6 carbon atoms, such as methanol, ethanol, propanol, isopropanol, butanol, pentanol, hexanol etc.

Any source of omega 9 series unsaturated fatty acids used can be used for the present invention. For example, a fatty acid can be obtained by microorganisms capable of producing an omega 9 series unsaturated fatty acid, animal tissues deficient in essential fatty acids, or culture animal cells deficient in essential fatty acids, or produced by chemosynthesis or enzymatic synthesis, or extracted and isolated from animal cartilage can be used. Particular microorganisms capable of producing an omega 9 series unsaturated fatty acid are, for example, microorganisms which have $\Delta 5$ desaturase activity and $\Delta 6$ desaturase activity and having reduced or lost $\Delta 12$ desaturase activity, such as *Mortiellela alpina* SAM 1861 (FERM BT-3590), as described in Japanese Unexamined Patent Publication No. 5-91888.

To extract and isolate free omega 9 series unsaturated fatty acids or esters thereof from the microorganisms, according to a conventional procedure, fat and oil extracted with an organic solvent such as n-hexane or supercritical carbon dioxide from the cultured microbial cells, and the fat and oil is subjected to hydrolysis and esterification to obtain a mixture of fatty acids or a mixture of fatty acid esters, and a desired 6,9-cis-octadecubienoic acid, 8-11-cis-eicosadienoic acid, 5,8,11-cis-eicosatrienoic acid etc. in a form of free fatty acid or fatty acid ester can be obtained by urea fractionation, liquid/liquid partition chromatography, column chromatography or the like in a purity of at least 80%.

More specifically, the extraction purification of fatty acid can be carried out according to a procedure as described in Japanese Unexamined Patent Publication No. 5-91888.

According to the present invention, not only highly purified fatty acid, but also a mixture of free fatty acids (including free omega 9 series unsaturated fatty acids), a mixture of fatty acid esters (including omega 9 series unsaturated fatty acid esters) or a fat and oil (including omega 9 series unsaturated fatty acids in form of a free fatty acid, mono-, di- or tri-glyceride, phospholipid, glycolipid, or amides) can be used. The fat and oil can be obtained by extracting from cultured microbial cells of microorganisms capable of producing an omega 9 series unsaturated fatty acid according to the above-mentioned method. The mixture of free fatty acids or the mixture of fatty acid esters can be obtained by isolating from the fat and oil according to the above-mentioned method.

The present composition for prophylaxis or improvement of medical symptoms caused by $LTB_4$ can be formulated from an omega 9 series unsaturated fatty acid and conventionally used carrier, excipient, additive etc., and can be used in oral or parenteral forms in the field of medicines, quasi-drug, cosmetics, foods or drinks.

The medical symptoms caused by $LTB_4$, to which the present invention is applied are, for example, inflammatory symptoms such as erythema and edema, hyperalgesia, ache, inflammatory symptoms resulting from alergic reaction, rheumatoid arthritis, chronic arthritic rheumatics, gout, psoriasis, infections, inflammatory bowel diseases, infusion damage, chronic long diseases, various arthritic symptoms, inflammatory symptoms accompanying asthma (for example, late stage hypersensitivity), collagen disease, allergic rhinitis, bronchial asthma, atopic dermatitis, tympanitis, urticaria, contact dermatitis, drug allergy, food allergy, insect allergy, arrhythmia, acute myocardial infraction, ischemia-reperfusion damage. Since the present fatty acids selectively inhibit the production of $LTB_4$, side effects are relatively small, and the fatty acids can be applied to chronic symptoms, and are useful for improvement of rheumatoid arthritis. In the present invention, the phrase "improvement of symptoms" is used in the broad sense, and includes treatment of a patient.

Where the present fatty acids are used in a pharmaceutical composition, they can be used in any formulations suitable for oral or parenteral administration, for example, injections, infusion, powders, granules, tablets, capsules, enteric coated tablets, enteric capsules, troche, mixture for internal use, suspension, emulsion, syrup, liquid for external use fomentations, nasal drops, ear drops, eye drops, inhalant, ointment, lotion, suppository etc. They may be used alone or in combination according to the symptom. These formulation may be prepared using a main component and conventional aids such as excipient, binder, disintegrator, lubricant, corrigent, and the like according to the purpose. An administration dose varies depending on the purpose of the administrations and conditions of a subject which receives the composition such as sex, age, weight etc., and usually, where the fatty acid is orally administered to an adult human, its daily does is 1 to 1000 mg, and preferably 1 to 500 mg, and more preferably 1 to 200 mg; and for parenteral administration, daily dose is 0.1 to 100 mg, and preferably 0.1 to 50 mg, and more preferably 0.1 to 20 mg.

It is known that fatty acids as active ingredients of the present invention are biosynthesized in-vivo under an essential fatty acid deficient condition. In addition, when the present fatty acids were continuously orally administered to IRC male mice of 7 weeks old at a dose of 2 g/day/kg for 2 weeks, abnormal symptom was not observed. Therefore, the present fatty acids are excellent in a safety point of view.

In the case where the present fatty acids are used in a form of foods or drinks, the fatty acids may be not only in a form of the above-mentioned formulation, but also may be added to a food stuff, especially, to a food stuff not containing the present omega 9-series unsaturated fatty acid, and a food may be manufactured according to a conventional procedure. The amount of fatty acids to be added to a food stuff varies depending on the nature of food, and preferably 0.001 to 50% relating to the total weight of the food, though it is not limited to this range.

Healthy foods or functional foods containing the present fatty acid are used for prevention or improvement of medical symptoms caused by $LTB_4$. The forms thereof may be not only the above-mentioned pharmaceutical formulations, but also may be processed foods such as liquid food, semi-digested nutrient food, component nutrient food, drinks incorporating, in addition to the present fatty acids, for example proteins, sugars, fats, minor elements, vitamins, emulsifier, perfume etc. As the above-mentioned proteins, are used milk protein, soybean protein, egg albumin, which have high nutrient value with good amino acid balance. In addition functional food in-situ prepared by adding the present fatty acid to a food may be provided to patients, in a hospital under control by a dietician according to a nutritional prescription prescribed by a doctor.

Foods containing the present fatty acid are preferably orally taken to an adult human in an amount which provides 1 to 1000 mg/day, and preferably 1 to 500 mg/day, and more preferably 1 to 200 mg/day of the fatty acid, for the purposes of prevention or improvement of medical symptoms caused by $LTB_4$, or for maintaining healthy condition.

The foods or drinks containing the present fatty acid may be foods or grocery items in a form of solid or liquid, for example, bread, noodle, rice, confectioneries such as biscuit, cake, candy, chocolate, Japanese sweets, agricultural food products such as soybean curd and derivatives thereof, fermentation products such as Japanese sake or medical beverage, sweet sake, vinegar, soy sauce, dressings, stock farm products such as yogurt, ham, bacon, sausage or mayonnaise, fish product such as boiled fish paste or fried fish paste, drinks such as juice, refreshing drink, sports drink, alcoholic drink, tea, and the like.

EXAMPLES

Now, the present invention is more specifically explained by Examples.

Example 1

To 10 g of an omega 9 series unsaturated fatty acid-containing triglyceride (containing 12.45% 6,9-cis-octadecadienoic acid, 3.65% 8.11-cis-eicosadienoic acid, and 14.44% 5,8,11-cis-eicosatrienoic acid) and 1.2 g of yolk phospholipid, was added 2.5% aqueous glycerol solution to make the total weight 100 g to prepare an emulsion. 5 rabbits (weighing 3.5 Kg) were injected with 30 ml of the emulsion through a tail vein, and before the injection (0 hour) and 6 hours from the injection, blood samples were obtained. The blood sample was mixed with the same volume of PBS, and polymorphonuclear leukocyte (PMNL) was obtained by a Ficoll-Conray overlay method. To the PMNL was added calcium ionophore A23187 to the concentration of 1 $\mu$g/ml, and $LTB_4$ produced was measured by reversed phase high performance liquid chromatography. The result is shown in Table 1.

TABLE 1

| Amount of $LTB_4$ produced (ng/$10^7$ PMNL) | |
|---|---|
| Before injection | 6 hours after injection |
| 16.9 | 8.1 |
| 20.8 | 9.5 |
| 24.4 | 19.3 |
| 14 5 | 2.4 |
| 15.9 | 1.5 |
| 18.50 ± 4.05[1] | 8.15 ± 7.14[2] |

[1]Mean ± Standard deviation
[2]$P < 0.05$

Example 2

10 g of 6,9-cis-octadecadienoic acid ethyl ester (95% purity) or 10 g of 8,11-cis-eicosadienoic acid ethyl ester (95% purity) or 10 g of 5,8,10-cis-eicosatrienoic acid ethyl ester (95% purity), and 1.2 g of yolk phospholipid were mixed, and 2.5% aqueous glycerol solution was added thereon to make the total weight 100 g, to prepare emulsion A, emulsion B or emulsion C, respectively. 3 ml of the emulsion A, B or C was injected to 5 rabbit (weighing 3.5 kg) through a tail vein, and before the injection (0 hour) and 6 hours from the injection, an amount of $LTB_4$ produced by polymorphonuclear leukocyte (PMNL) was measured according to the same procedure as described in Example 1. The result is shown in Table 2.

TABLE 2

| | Amount of $LTB_4$ produced (ng/$10^7$ PMNL) | |
|---|---|---|
| Emulsion | Before injection | 6 hours after injection |
| A | 18.96 ± 3.89 | 13.06 ± 2.91* |
| B | 18.30 ± 3.56 | 9.88 ± 2.33** |
| C | 20.36 ± 3.45 | 6.86 ± 3.31** |

Mean ± Standard deviation
*P < 0.05
**P < 0.01

As can be seen from the above, the emulsions A, B and C significantly inhibited the production of $LTB_4$, and especially inhibitory action of the emulsion C(containing 5,8,11-cis-eicosatrienoic acid ethyl ester) is excellent.

Example 3

Male Wister rats, 5 weeks old, were divided into two groups each consisting of 6 rats. The first group received a feed composed of 90% of lipid-free powder diet, 8% of lard and 2% of omega 9 series unsaturated fatty acid-containing triglyceride (containing 19.99% 6,9-cis-octadecadienoic acid, 2.00% 8,11-cis-eicosadienoic acid and 18.62% 5,8,11-cis-eicosatrienoic acid). Another group received a feed composed of 90% of lipid-free powder diet, 8% of lard and 2% of soybean oil. After 15 days, 0.1 ml of a saline containing 1% (W/N) carrageenin (Type IV, Sigma Chemical Co., St. Louis, Mo.) was injected into the right hind foot pad of each rat, and 4 hours later a swelling ratio was calculated from a measurement of the footpad volume according to the following equation.

$$\text{Swelling ratio} = \frac{\text{Swollen value} - \text{Original value}}{\text{Original value}} \times 100$$

Swelling ratio for the group which received omega 9 series fatty acid-containing triglyceride was 44.6±4.3%, while that for the group which received soybean oil was 61.0±11.3%. Therefore, the swelling ratio was significantly reduced (P<0.05) by administration of omega 9 series unsaturated fatty acids.

Example 4

180 mg of 5,8,11-cis-eicosatrienoic acid ethyl ester was filled into a soft capsule shell composed of the following components:

Gelatin 70.0%
Glycerine 22.9%
Methyl paraoxybenzoate 0.15%
Propyl paraoxybenzoate 0.51%
Water valance
Total 100%
to obtain a soft capsule.

Example 5

2 g of β-cyclodextrin was added to 20 ml of 20% ethanol aqueous solution, and 100 mg of 5,8,11-cis-eicosatrienoic acid ethyl ester was added thereon while stirring the mixture with a stirrer, and the mixture was incubated at 50° C. for 2 hours. After cooling to a room temperature (for about 1 hour), the mixture was further incubated at 4° C. for 10 hours while stirring. Resulting precipitate was recovered by centrifugation, washed with n-hexane, and lyophilized to obtain 1.8 g of cyclodextrin inclusion compound containing 5,8,11-cis-eicosatrienoic acid ethyl ester. 1 g of this powder was homogeneously mixed with 10 liters of juice to prepare 5,8,11-cis-eicosatrienoic acid ethyl ester-containing juice.

Example 6

An animal test was carried out according to a method of T. S. Courtensy (Nature 283, 666, 1980) with slightly modification. Namely, DBA/lJNCrj mice, 7 week old, weighing 20 g (Charles River Japan Inc.) were used. One group consisted of 10 mice. For antigen preparation, 0.3% bovine type II collagen (Collagen Gijutsu Kenshukai) was emulsified with a equal volume of Freund's complete adjuvalent (INC Biomedica Inc.) Each mouse was injected intradermally on the root of tail with 0.1 ml of the antigen preparation. After 14 days from the injection, each mouse was boosted by intraderml injection with bovine type II collagen (Collagen Gijutsu Kenshukai) emulsified with Freund's incomplete adjuvant (DIFCO) at the same volumes to generate arthritis.

The test group orally received 1 mg/kg of a mixture of mead acid (comprising 90.1% and acid ethyl ester 7.9% 6,9-cis-octadecadienoic acid ethyl ester, 1.4% oleic acid ethyl ester, 0.6% arachidic acid ethyl ester) (mixed in olive oil 200 μl per mouse) and the control group orally received olive oil (200 μl) 5 times per week, starting at the seventh day from the first immunization. The positive control group received auranofin (10 mg/kg, intraperifoneal administration, Smith Kline Beecham Seiyaku).

The severity of arthritis was scored as follow (designated as RAscore, 0 to 4 point for one paw, at most 16 point in total for four paws). Namely, point 0: no change point 1: weak swelling and weak reddish, point 2: weak swelling and reddish, point 3: strong swelling and reddish, point 4: storing swelling accompanied with deformation of bone and reddish were used as a evaluation standard. As a result, administration of mead acid (1 mg/kg) provided decrease of the RAscore, and arthritis was improved. The decreasing effect was about 30% on the 35th day from the second immunization, which was the same as the positive control group which received auranofin. A result is shown in FIG. 1.

We claim:

1. A method for the prevention or treatment of allergy caused by leucotriene B4 (LTB4) in a patient in need thereof comprising administering to said patient an omega 9 series unsaturated fatty acid, wherein said omega 9 series unsaturated fatty acid is at least one of 6,9-octadecadienoic acid, 8,11-eicosadienoic acid or 5,8,11-eicosatrienoic acid, in an amount effective for preventing or treating said allergy.

2. The method according to claim 1, wherein the omega 9 series unsaturated fatty acid is 6,9-octadecadienoic acid.

3. The method according to claim 1, wherein the omega 9 series unsaturated fatty acid is 8,11-eicosadienoic acid.

4. The method according to claim 1, wherein the omega 9 series unsaturated fatty acid is 5,8,11-eicosatrienoic acid.

5. The method according to claim 1, wherein 6,9-octadecadienoic acid, 8,11-eicosadienoic acid and 5,8,11-eicosatrienoic acid are administered.

6. The method according to claim 1, wherein the omega 9 series unsaturated fatty acid is orally or parenterally administered.

7. The method according to claim 6, wherein the omega 9 series unsaturated fatty acid is orally administered in an amount of between about 1 to 1000 mg per day.

8. The method according to claim 7, wherein the omega 9 series unsaturated fatty acid is orally administered in an amount of between about 1 to 500 mg per day.

9. The method according to claim 8, wherein the omega 9 series unsaturated fatty acid is orally administered in an amount of between about 1 to 200 mg per day.

10. The method according to claim 6, wherein the omega 9 series unsaturated fatty acid is orally administered in an amount of between about 0.1 to 100 mg per day.

11. The method according to claim 10, wherein the omega 9 series unsaturated fatty acid is orally administered in an amount of between about 0.1 to 50 mg per day.

12. The method according to claim 11, wherein the omega 9 series unsaturated fatty acid is orally administered in an amount of between about 0.1 to 20 mg per day.

13. A method according to claim 1, wherein the allergy is rheumatoid arthritis.

14. A method for the prevention or treatment of allergy caused by leucotriene B4 (LTB4) in a patient in need thereof comprising administering to said patient a food or drink which comprises an omega 9 series unsaturated fatty acid, wherein said omega 9 series unsaturated fatty acid is at least one of 6,9-octadecadienoic acid, 8,11-eicosadienoic acid or 5,8,11-eicosatrienoic acid, in an amount effective for preventing or treating said allergy.

15. The method according to claim 14, wherein the omega 9 series unsaturated fatty acid is 6,9-octadecadienoic acid.

16. The method according to claim 14, wherein the omega 9 series unsaturated fatty acid is 8,11-eicosadienoic acid.

17. The method according to claim 14, wherein the omega 9 series unsaturated fatty acid is 5,8,11-eicosatrienoic acid.

18. The method according to claim 14, wherein 6,9-octadecadienoic acid, 8,11-eicosadienoic acid and 5,8,11-eicosatrienoic acid are administered.

19. The method according to claim 14, wherein the omega 9 series unsaturated fatty acid is present in an amount of from 0.001 to 50% by weight of the total food or drink.

20. A method according to claim 14, wherein the allergy is rheumatoid arthritis.

* * * * *